US 6,312,439 B1
Nov. 6, 2001

(54) REFRACTION CORRECTION WITH CUSTOM SHAPING BY INNER CORNEAL TISSUE REMOVAL USING A MICROJET BEAM

(75) Inventor: Eugene I. Gordon, Mountainside, NJ (US)

(73) Assignee: Medjet, Inc., Edison, NJ (US)

( * ) Notice: Subject to any disclaimer, the term of this patent is extended or adjusted under 35 U.S.C. 154(b) by 0 days.

(21) Appl. No.: 09/483,687

(22) Filed: Jan. 14, 2000

Related U.S. Application Data

(60) Provisional application No. 60/137,242, filed on Jun. 2, 1999, and provisional application No. 60/115,966, filed on Jan. 15, 1999.

(51) Int. Cl.⁷ .................................. A61B 17/32
(52) U.S. Cl. ........................................... 606/166
(58) Field of Search .................... 606/166, 167, 606/174, 4, 5, 6, 1; 128/898; 604/22

(56) References Cited

U.S. PATENT DOCUMENTS

| | | |
|---|---|---|
| 3,058,471 | 10/1962 | Shope .................................. 128/305 |
| 3,074,407 | 1/1963 | Moon et al. ........................ 128/303 |
| 3,129,971 | 4/1964 | Kobler ................................. 294/64 |
| 3,139,298 | 6/1964 | Grabiel ................................. 294/1 |
| 4,024,866 | 5/1977 | Wallach . |
| 4,077,411 | 3/1978 | Ward .................................. 128/303 |
| 4,236,519 | 12/1980 | La Russa et al. .................. 128/305 |
| 4,660,556 | 4/1987 | Swinger et al. .................... 128/305 |
| 4,662,370 | 5/1987 | Hoffmann et al. . |
| 4,744,362 | 5/1988 | Grundler . |
| 4,936,850 | 6/1990 | Barrett . |
| 5,318,046 | 6/1994 | Rozakis . |
| 5,556,406 | * 9/1996 | Gordon et al. ..................... 606/167 |
| 5,626,594 | 5/1997 | Smith . |
| 5,643,299 | 7/1997 | Bair . |
| 5,833,701 | 11/1998 | Gordon . |
| 6,143,011 | 11/2000 | Hood et al. . |

* cited by examiner

Primary Examiner—Kevin Truong
(74) Attorney, Agent, or Firm—Darby & Darby

(57) ABSTRACT

The present invention provides a new approach to reshaping of the cornea, e.g., for refraction change, using multiple, displaced planar cuts and a custom shaping template. Large refractive change and/or substantial tissue removal can be obtained by a two-cut approach to reshaping of the cornea to a desired shape using a template or applanator. The process begins with a planar template being applied to the cornea. The template includes one or more moveable sections or cams positioned to provide an overall flat contact surface with the cornea. Then, a first cut is made by a water microjet producing a hinged flap. The first cut is parallel to but displaced from the anterior cornea surface in contact with the template. Then the template cam or cams are repositioned to change the shape of the cornea surface in situ in preparation for the second cut. The hinged flap is not moved; it remains in contact with the stromal bed. The second cut is along the same path as the first cut. However, since the cornea has been reshaped, the second cut defines a separate cut line in the cornea. As a result of the first and second cuts, a body of internal tissue defined by the relative paths of the first and second cuts through the corneal tissue can be removed from the cornea to thereby shape the cornea and provide refractive correction. This enables a large range of accurate refractive correction and/or therapeutic tissue removal by directly controlling the geometry of the volume of tissue removed from the interior of the cornea.

15 Claims, 6 Drawing Sheets

REFRACTION CORRECTION WITH CUSTOM SHAPING BY INNER CORNEAL TISSUE REMOVAL USING A MICROJET BEAM

This patent application claims priority of U.S. Provisional Patent Applications Nos. 60/115,966 filed on Jan. 15, 1999 and entitled "Refraction Collection by Inner Corneal Tissue Removal Using A Microjet Beam" and Ser. No. 60/137,242 filed on Jun. 2, 1999 and entitled "Refractive Correction Microjet Keratome With Custom Shaping." Each of Provisional Applications Nos. 60/115,966 and 60/137,242 is incorporated in its entirety by reference into this specification.

FIELD OF THE INVENTION

The present invention relates to refraction correction in general and, more particularly, to refractive correction involving a shaping template and a fluid microjet applied to the cornea to cut tissue.

BACKGROUND OF THE INVENTION

Reshaping of the cornea for refractive vision correction has been the object of various procedures, some of which have only been recently developed. In one well known procedure, namely, radial keratectomy (RK), the cornea is incised with radial cuts to flatten the shape of the anterior surface of the cornea in order to correct for myopia. This is a surgical procedure requiring a high degree of skill and judgment for effective and safe implementation.

Additionally, even when such procedure is carried out properly, myopia-corrective flattening may cause instabilities, such as a gradual progression to hyperopia over time.

Another recently developed system uses an chimer laser to remove corneal tissue by photo-thermal ablation rather than cutting. In the latest version of this system, a sequence of incident laser pulses with energy focused to a small spot moving from point to point gradually removes tissue from the anterior surface of the cornea. The local extent of tissue removal depends on the number of laser pulses at the position on the cornea and results in a new shape for the ablated surface. An eye tracker is used in some versions to compensate for eye motion during the lengthy scan period, e.g., tens of seconds. Laser spot scanners utilize a bell-shaped laser energy distribution having a half-power diameter of about 2 mm. It is likely that smaller laser spots could be achieved, but stability of the eye or accuracy of the eye tracker may limit the useful resolution. The pulsed delivery of laser energy in spots and arbitrary spot positioning allows overlap during scanning for smoothing. The equivalent spot density can be high. Nevertheless, the achievable resolution or shaping detail is limited by the spot size, since overlapped spots are not independent. Also, the spatial frequency transfer function for patterning effects the accuracy of the laser spot scanners. Based on the 2 mm spot size, the distribution is probably flat out to a cutoff spatial frequency of about 0.25 cycles/mm. Over a 6 mm ablation zone, that implies only 1.5 cycles of shaping. It seems barely enough for myopic correction. For hyperopic correction, a 9 mm zone would be required. It may not be enough for achieving super acute vision where finer features need to be resolved.

This use of laser pulses for shaping the cornea, known as photo-refractive keratectomy (PRK) is generally safe and effective. However, there are several drawbacks to this method, including the high cost of the equipment required for the PRK procedure. Another drawback is the relatively high residual error factor (or lack of emmetropia), often on the order of ±1.0 diopter more, as compared to a typical error of less than ±0.25 diopter for spectacles or contact lenses. In addition, laser ablation results in a rough corneal surface. Furthermore, there are long term effects relating to the physiology of the cornea and its interaction with the laser during ablation, which may result in subsequent gradual reversal of the correction and/or complications due to wound healing and/or potential carcinogenic effects. Other common side effects of PRK include haze, night-time glare and reduced best-corrected visual acuity.

The cornea comprises a thin protective epithelium layer on top of the Bowman's membrane or layer, which in turn covers the major corneal stroma. While the epithelium is regenerative, the Bowman's membrane is not. With ablative corneal tissue removal procedures such as PRK, the epithelium and Bowman's membrane are removed together with a portion of the stroma. Subsequently, the epithelium regenerates on the exposed outer surface of the cornea directly on the stroma because the Bowman's layer is not regenerated. However, direct regrowth of the epithelium on the stroma can cause an undesirable corneal haze which gradually dissipates over time.

Both the RK and PRK methods described above have inherent instabilities and error factors which make them generally unsuitable for correction of myopia of more than −9 diopters. A surgical procedure known as Automated Lamellar Keratoplasty (ALK) preserves the Bowman membrane and has been used for corrections of up to −20 diopters. In this procedure, in a first surgical step, a blade micro-keratome is used to remove a uniform thickness button or lenticule of corneal tissue which contains a portion of the epithelium layer, the Bowman's membrane (intact) and a portion of the stroma. The button or lenticule preferably remains "hinged" at one point to the cornea. The hinged lenticule is then moved out of the way and the stromal bed is surgically reshaped with the micro-keratome by removal of a second unhinged lenticule to produce the required refraction correction. Then, the hinged lenticule is replaced on the stromal bed, providing good adherence and healing of the stroma-stroma interface, preserving the Bowman's membrane, and leaving the cornea substantially clear. It appears that the stroma-stroma healing of the ALK procedure reduces, if not eliminates, wound healing instabilities, making this procedure suitable for large refractive corrections.

However, despite the advantage of retention of vision clarity and healing stability, the ALK procedure is not favored because it is complex and expensive, requires high surgical skills and, depending on the surgeon's skill, is usually inaccurate and may cause irregular astigmatism. Some of these problems may be attributed to the viscous and generally unsupported nature of the cornea, which may be enhanced by reflexive movements of the patient, making the use of a scalpel or even a micro-keratome difficult and inaccurate.

In view of the above, currently the most favored approach to refraction correction is to produce a hinged flap with a blade micro-keratome and then to reshape the exposed stromal bed using PRK as described above. This procedure, commonly referred to as LASIK, is less safe than conventional PRK and is used primarily because of reduced short-term inconveniences, such as pain and delay in return of visual acuity. The long term effects of LASIK are similar to those of PRK.

Cleaving off a lenticule having a predetermined shape using a microjet beam is also known in the art. Such a procedure is described in U.S. Pat. No. 5,556,406 to Gordon et al., the entire disclosure of which is incorporated herein by reference. In practice, a number of different procedures using a microjet beam have been applied for refraction correction.

In a procedure known as the HRK1, by Medjet Inc. (Edison, N.J.), a lenticule having a desired shaped is removed by a microjet beam. After this removal, epithelium growth on the remaining stromal bed may change the optical properties of the cornea causing inaccuracies in the refraction correction. This phenomenon is similar to that described above with reference to PRK. Another procedure using a microjet beam, known as HRK2, is similar to the two-step ALK technique described above. In a first step, a microjet beam cut is used to form a hinged flap in the cornea. The flap is then moved to the side and a second cut is made with the microjet beam, removing a lenticule of a predetermined shape for refractive correction. Finally, the flap is replaced in its original position. The results are similar to those of the ALK technique, but the use of a water jet beam is safer and more accurate. This technique is described in U.S. Pat. No. 5,556,406 to Gordon et al.

By investigating the interaction of a fluid microjet beam with the cornea, the present inventors have discovered that a single lamellar cut in the cornea can be used to remove inner corneal tissue under a parallel flap. When the flap is placed back on the cutting site, the resultant corneal surface is flattened compared to the original surface topography.

In a procedure known as HRK3 by Medjet Inc., shaping of the cornea by erosion and cutting a hinged flap are preformed simultaneously. According to experimental results, a surface cut by fluid microjet cannot be distinguished, under microscopic examination, from a surface cleaved by a micro-keratome. Shaped erosion removal of tissue is also possible under certain scan conditions. Experimental results also indicate that HRK tissue removal can result in a spherical surface. The thickness of removed tissue is less than or greater than the microjet beam diameter, as required. However, based on experimental results, there seems to be a practical limit to the thickness of tissue that may be removed by a single beam scan and, thus, there is a limit to the refractive change that may be achieved by this method. In general, erosion tissue removal can be increased by reducing the scanning speed of the microjet beam; however, substantial slowing of the scanning speed results in poor or even unacceptable surface quality. This technique is described in U.S. patent application Ser. No. 08/955,645, filed Oct. 22, 1997, the entirety of which is incorporated by reference. To achieve greater refraction correction by erosion shaping, a multi-scan technique has been used, wherein a high accuracy scanning robot performs multiple scans in the same plane for additional tissue removal by erosion. In this technique, greater tissue removal can be achieved by cutting and, thus, greater diopter correction. However, multiple scanning of the microjet beam is similar to slow scanning of the beam and may therefore result in poor surface quality.

Therefore, the rapid evolution of refractive surgery based on the LASIK procedure and the increasing interest in the potential of a surgical approach to achieve super acute vision has created an interest in a surgical procedure which will allow accurate and high resolution custom tissue removal. Improved refraction correction results compared to the surgical procedures described above are needed.

SUMMARY OF THE INVENTION

The present invention provides a new approach to reshaping of the cornea, e.g., for refraction change, using multiple, displaced planar cuts and a custom shaping template. In accordance with an embodiment of the present invention, large refractive change and/or substantial tissue removal can be obtained by a two-cut approach to reshaping of the cornea to a desired shape using a template or applanator. More particularly, a water microjet is used to shape the cornea by two successive co-planar cuts in the cornea. For example, the process begins with a planar template being applied to the cornea. The template includes one or more moveable sections or cams positioned to provide an overall flat contact surface with the cornea. Then, a first cut is made by the microjet producing a hinged flap. The first cut is parallel to but displaced from the anterior cornea surface in contact with the template. Then the template cam or cams are repositioned to change the shape of the cornea surface in situ in preparation for the second cut. The hinged flap is not moved; it remains in contact with the stromal bed. The second cut is along the same path as the first cut. However, since the cornea has been reshaped, the second cut defines a separate cut line in the cornea. As a result of the first and second cuts, a body of internal tissue defined by the relative paths of the first and second cuts through the corneal tissue can be removed from the cornea to thereby shape the cornea and provide refractive correction. This enables a large range of accurate refractive correction and/or therapeutic tissue removal by directly controlling the geometry of the volume of tissue removed from the interior of the cornea.

In accordance with one embodiment of the present invention, a body of inner corneal tissue is removed by first and second successive cuts in the cornea, the first cut producing a hinged flap of corneal tissue and the second cut being made without lifting the anterior flap of tissue and without otherwise moving, repositioning and/or realigning the cornea between the first and second cuts. The shape of the template is changed between the first and second cuts. In the alternative, the microjet beam can be moved but changing the shape of the template is easier than moving the beam.

In accordance with a preferred embodiment of the invention, a first lamellar cut is made by scanning a microjet beam across the cornea while the cornea is subjected to a predefined planar applanation by a template which maintains a flat shape of the cornea. After completing the first cut, the microjet can be scanned back to its starting position, typically with the microjet beam deactivated and without lifting or otherwise moving the parallel flap produced by the first lamellar cut. At this point, the template shape can be changed to a predetermined configuration, causing the anterior surface of the cornea to assume a new predetermined shape. Then, the waterjet beam is reactivated and a second scanning of the waterjet in the same plane is performed, producing a second cut in the corneal tissue. Relative to the corneal tissue, the second cut is displaced with respect to the first cut and, thus, a body of tissue defined by the relative paths of the first and second cuts is ejected during the second scanning of the microjet. The ejection of such body of tissue, which resembles a thin slab, has been viewed experimentally. The volume of the ejected tissue is generally responsive to the difference in shape of the anterior surface between the first and second cuts due to a change in the template configuration and/or a difference in position of the scanning beam relative to the cornea. By changing the shape of the cornea between cuts, the technique of the present invention can be used for refraction collection applications. Alternatively, the order of the template positions described above can be reversed such that the first template configuration is non-planar and the second template configuration is planar. Furthermore, by changing the scanning position or plane of the microjet beam between cuts, the technique of the present invention can be used for other ophthalmic application, such as removal of defects in the cornea, without refraction correction. In this case, a parallel slab is removed.

Another embodiment of the present invention further provides a device for variably controlling the shape of the anterior surface of the cornea. In an embodiment of the present invention, the device includes a variable vacuum template to support the anterior surface of the cornea in different shapes, while continuously engaging the cornea. This device is capable of changing the shape of the anterior surface of the cornea between the first and second cuts of the technique described above. The shape is changed based on the use of one or more cams or pistons as part of the template. The cams can provide a flat surface for contact with the anterior cornea surface for the first cut and a different shape (e.g., a convex or concave shape relative to the slope of the corneal surface etc.) for repositioning the anterior cornea surface for the second cut.

In accordance with another feature of the invention, the template shape has the following operating specifications: the shaping resolution has a falloff spatial frequency of 0.5 cycles/mm or approximately twice the resolution of prior art laser devices. This implies that the linear density of controlled, independent tissue incision zones should be at least 1 per mm. It should be possible to remove no tissue at one point and to remove 100 $\mu$m of tissue at any adjacent point distant by 1 mm. As a result, a smooth gradation is provided and the tissue incision zones fall within particular diameter circles to accommodate particular corrections. For example, a tissue incision zone falling within a 9 mm diameter circle accommodates hyperopic correction while a tissue incision zone falling within a 6 mm diameter circle accommodates myopic correction. In addition, the maximum thickness of the lamella layer, the tissue removal aliquot, is set to ±2 microns based on the following analysis: the photo-ablation depth of laser shapers is not really under good control. In a given cornea, the photo-ablation rate is dependent on many factors: the particular cornea, the surface preparation, the thickness of the flap, the level of hydration, the temperature, etc. Moreover, the pulse power varies from pulse to pulse, perhaps as much as ±20%. Although ambient temperature and humidity play a role, they are usually not well controlled in the surgical suite. In terms of results, the breadth of the distribution of initially achieved refractive correction versus intended correction is greater than ±1 diopter. For myopia correction of a plano-convex volume having a diameter of 6 mm, the refractive power is ±1 diopter for each 13mm of thickness at the center of the volume. This suggests that the tissue removal accuracy at the center of a 6 mm diameter circle is not better than ±13 $\mu$m. As a result, ±2 microns, about the maximum thickness of a lamella layer, the tissue removal aliquot, is the objective using the template. This would provide an accuracy of ±⅙ diopter.

The preferred embodiment of the present invention uses a liquid microjet as the scanned fluid beam for implementing the refractive correction techniques using multiple displaced cuts. A liquid microjet is described in U.S. Pat. No. 5,556,406.

DETAILED DESCRIPTION OF PREFERRED EMBODIMENTS

Figure 1:
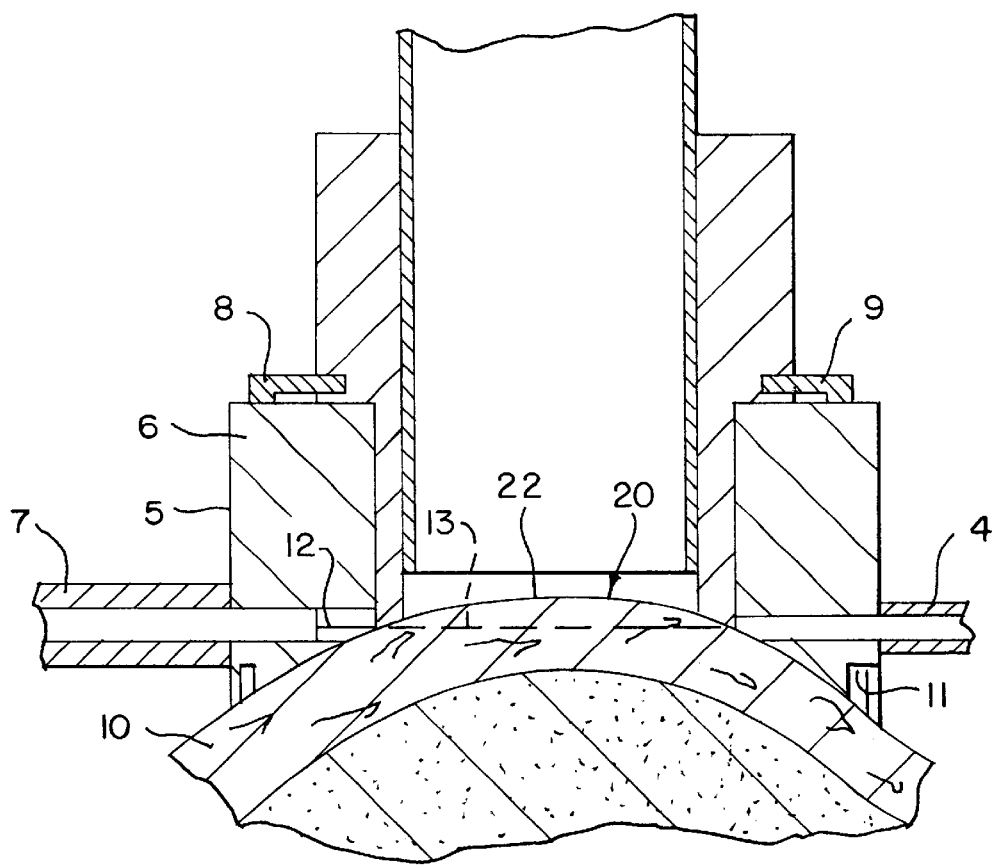
FIG. 1 is a schematic side view illustration of an arrangement for removal of corneal tissue using a microjet beam and a vacuum template in accordance with an embodiment of the present invention.

FIG. 1 schematically illustrates a side-view cross section of an arrangement for removing inner layer tissue from a cornea 10 using a microjet beam 12 and a vacuum template 20 in accordance with an embodiment of the present invention. The general structure and operation of the arrangement of FIG. 1, except for the specific structure and operation of template 20, described in detail below, arc generally analogous to FIG. 4 of U.S. Pat. No. 5,556,406, wherein similar elements perform similar functions, except as described below. Vacuum template 20 may be electronically controlled to provide a predetermined configuration which maintains the anterior surface 22 of cornea 10 in a predetermined shape, which may differ depending on the desired refraction correction being performed, e.g., correction for myopia, hyperopia, astigmatism and/or any other desired refraction correction presently known or hereinafter discovered. In some embodiments of the invention, to accommodate different configurations for cornea 10, template 20 includes a plurality of sub-templates (shown in FIGS. 4 and 8–11), which may be movable relative to each other and/or relative to cornea 10, to enable control of the physical shape of template 20 in addition to or instead of controlling the vacuum applied by the template.

As further shown in FIG. 1, the microjet cutting guide 5 is positioned relative to the template 20 such that the microjet beam 12 is aligned and coincident with the intended plane to be cut by such beam 12. The microjet cutting guide 5 is in the form of a ring 6, and the liquid microjet inlet 7 provides high-pressure liquid to the beam 12 to exit at the liquid microjet outlet 4. Template 20 is concentrically placed within the ring 6 and locked into position by locking tabs 8 and 9. To ensure that the deformation is effective in making the planar surface a true surface for cutting (i.e., wherein, after the cutting, the cornea relaxes into the desired configuration), a vacuum is applied through the porous template to cause the cornea surface 22 to conform closely to the template 20. The vacuum can be maintained until at least the intended cut is completed. The scan speed is preferably greater than 15 mm/sec to avoid erosion. Slower scan speeds are within the scope of the invention. The pump stagnation pressure is preferably high enough for the microjet to cut a full flap that's approximately 9 mm at maximum scan speed. An exemplary pressure is 20,000 psi with a beam diameter of 33 $\mu$m.

In accordance with the invention, as described in detail below, microjet beam 12 is activated and scanned to produce two cuts in cornea 10, such as cut 13, while vacuum template 20 maintains cornea 10 in a predetermined shape and position with respect to beam 12 during each of the two cuts. When two cuts arc made at two different configurations, as described below, a slab of inner corneal tissue of a predetermined shape is removed from cornea 10.

Figure 2A:
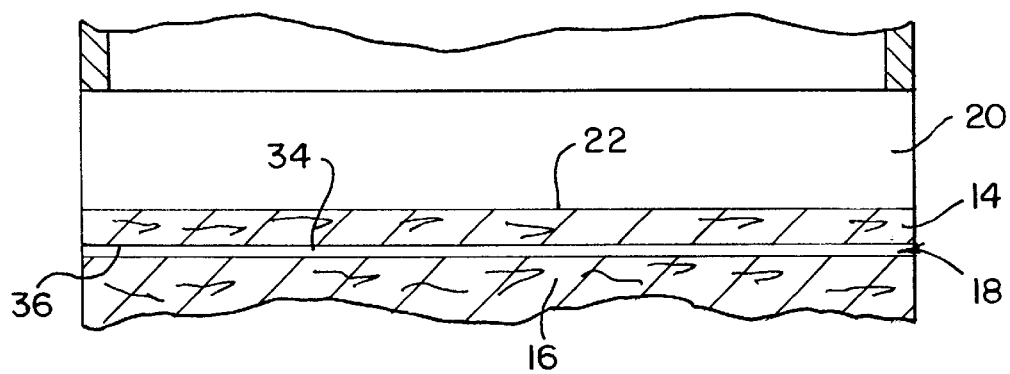
FIG. 2A is a schematic, side view, cross-sectional illustration of part of a cornea engaged by a substantially flat vacuum template after cutting a substantially parallel inner slab of corneal tissue using a microjet beam in accordance with the FIG. 1 embodiment of the present invention.
Figure 2B:
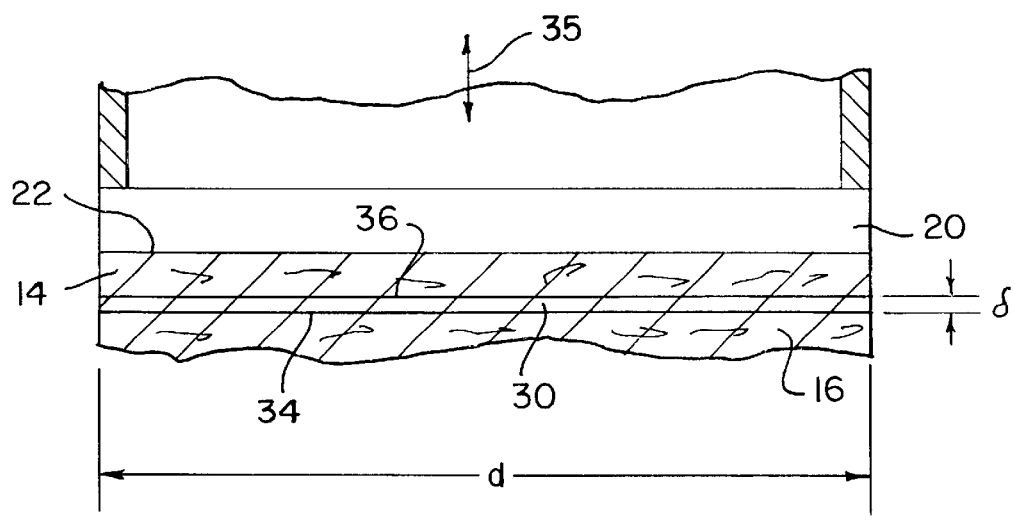
FIG. 2B is a schematic, side view, cross sectional illustration of part of the cornea and the fixed vacuum template of FIG. 2A showing cutting lines for removing the parallel slab of corneal tissue in accordance with the FIG. 1 embodiment of the present invention.

FIGS. 2A and 2B schematically illustrate a method for removal of inner corneal tissue using a microjet beam 12 in accordance with one embodiment of the invention. In the method of FIGS. 2A and 2B, a substantially flat template 20 is used whereby a slab of tissue 30 (shown in FIG. 2B) having substantially parallel surfaces is removed from cornea 10. Slab 30 is excised based on the anterior surface 22 of the cornea 10 contacting the template and the microjet beam (not shown) applying a first cut 36 followed by a second cut 34. In contrast to multiple scanning techniques in which the beam is used for erosion shaping (as shown, e.g., in U.S. Pat. No. 5,964,775 to Gordon et al., which is incorporated in its entirety into this specification), the method of the present invention relies on first and second cuts, 36 and 34, respectively, in FIGS. 2A and 2B, wherein the relative paths of cuts 34 and 36 are not coincidental by virtue of a template. Due to the non-coincidental cuts, in contrast to prior art cut techniques, a volume of corneal tissue not connected to adjacent tissue is produced and at least one macroscopic piece (slab) 30 of inner corneal tissue is ejected from cornea 10 as the second cut 34 is completed. In the exemplary embodiment of FIGS. 2A and 2B, the two cuts are substantially parallel and the plane of the second cut 34 is below the plane of the first cut 36, so that a substantially parallel slab 30 having a width $\delta$ is removed. Slab 30 forms a shallow cavity 18 (shown in FIG. 2A) having substantially parallel walls. Cavity 18 separates cornea 10 into an upper flap portion 14 and a lower stromal bed portion 16. Because a parallel flap is removed, this procedure produces substantially no refractive correction, in contrast to other procedures of the invention as described below. The procedure of FIGS. 2A and 2B is thus useful, inter alia, for removing internal defects in the cornea and other ophthalmic applications for which no refractive correction is necessary. The procedure of FIGS. 2A and 2B can be combined with procedures as described below to produce refraction correction in combination with other applications, such as removal of internal defects, e.g., by removing a non-parallel slab of a predefined thickness and shape.

In an embodiment of the present invention, the microjet beam is scanned, e.g., by a scanner robot, at very high speed, for example, 20 millimeters per second, with high accuracy. Thus, if the position of the microjet beam is not changed, the physical plane of the second cut is virtually identical to that of the first cut. Cavity 18 may be produced by merely changing the plane of the second microjet cut relative to the cornea. Alternatively, in embodiments of the present invention as described below, the shape and size of the removed inner corneal tissue arc controlled, for example, by controlling the configuration produced by vacuum template 20.

To measure the effect of corneal shaping on the resultant shape of the cornea after removal of the slab 30, the present inventors used varying weights in earlier experiments, e.g., up to a few hundred grams, on the support stricture of the template 20 after performing the first cut 36 and before performing the second cut 34. This displaced the template in the direction perpendicular to its plane by small amounts without changing the plane of the microjet cut. These experiments indicate that the relative displacement between the first and second cut is very small (a vertical displacement on the order of tens of microns of the plane of the second cut 34 relative to the plane of the first cut 36 is possible by a corresponding displacement of template 20; such vertical displacement of template 20 (e.g., upwards) is indicated by arrow 35 in FIG. 2B). Integral slabs are ejected after the second cut.

In accordance with experiments performed by the present inventors, an average central thickness of approximately 13 $\mu$m per diopter, for a removed plano-convex slab having a diameter of 6 mm, is required for typical refraction correction of myopia. This thickness per diopter is generally proportional to the diameter squared of the removed slab 30, as shown in FIG. 2B as the thickness $\delta$ and the diameter d of the slab 30, where $\delta$ is proportional to $d^2$. After completion of the above described procedure, cornea 10, including lower portion 16 and flap portion 14 thereon, is released from engagement with template 20, whereby flap 14 assumes its normal position. At this point, the sphericity of cornea 10 is substantially restored but the new spherical surface assumes a different curvature which corresponds to the desired refractive change. In addition, in order to obtain a controlled refractive change, the central thickness $\delta$ (shown in FIG. 2B) of the removed slab 30 must be accurately controlled, for example, with a maximum error of a few micrometers. The structure of the stroma and the physical processes related to cutting of the cornea impose a theoretical limit on the dimensional accuracy of the cutting, typically on the order of ±2 µm.

Figure 3:
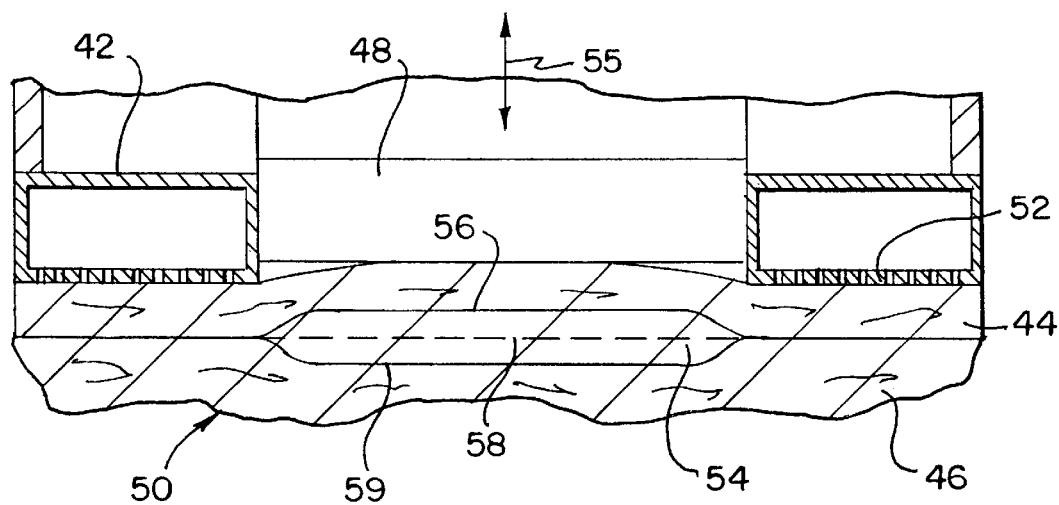
FIG. 3 is a schematic, side view, cross sectional illustration of part of a cornea and a vacuum template configured for cutting a slab of corneal tissue shaped for correction of myopia in accordance with an alternative embodiment of the present invention.

FIG. 3 shows a template arrangement generally suitable for use in correction of myopia. In this embodiment of the invention, template arrangement includes a fixed, annular, vacuum template 42 and a movable, central vacuum template 48 to provide a desired displacement between a first cut 56 and a second cut 54 made in a cornea 50 having an anterior surface 52 which contacts template elements 42 and 48. The illustrated template arrangement is merely an example and various other arrangements may yield similar results. For example, annular template element 42 may be movable and central template element 48 may be fixed, or both template elements may be movable to provide more flexibility in controlling the shape of anterior surface 52 of cornea 50 and, thus, more accurate refraction correction.

In the embodiment of FIG. 3, the position of central template element 48 is accurately adjusted and controlled, using means which are known in the art, while the plane of fixed template element 42 remains unchanged between the first and second cuts. During the scanning which forms first cut 56, performed prior to the situation shown in FIG. 3, template elements 42 and 48 are set to be substantially in the same plane and cornea 50 is divided into a stromal bed portion 46 and a parallel, yet applanated, flap portion 44. The boundary between these two parts of the cornea is defined by the plane of the first cut 56.

After the first cut 56 is complete, central template element 48 is displaced upwards (anteriorly) a predetermined distance, along the axis indicated by the upward arrow along axis 55. This allows the interface between stromal bed portion 46 and flap portion 44 to move upwards, as indicated by the broken line which designates the displaced path of first cut 56. The interface is displaced only in a predefined central area, due to the fixed annular template element 42. The amount of upward extension is responsive to the amount of upward displacement of moveable template element 48. Because the cornea is applanated, the natural direction of motion of the corneal tissue is upward when the constraint of template element 48 is removed. Thus, when a second cut 54 is performed in the same plane as the first cut 56, a slab of stromal tissue 58 extending above the cutting plane in the central region, is cleaved away.

Due to the speed of the scanning microjet beam during the second cut, slab 58 is ejected from cornea 50 without requiring any further steps. This surprising aspect of the present invention has been determined experimentally, as described above. Thus, as the second cut is performed, the slab of tissue 58 between the paths of first cut 56 and second cut 54 is separated from stromal bed 46 and is blown away by the scanning waterjet. In this manner, a shaped interior section of tissue is removed from the stroma. This results in controlled flattening of the cornea when the cornea including the flap and the stromal bed resumes its natural disposition after the template is removed. If the excised tissue 58 is designed to be elliptical, correction for astigmatism is also possible.

In another embodiment of the invention (shown in FIGS. 9–12), a more precise shaping of the tissue to be excised may be achieved by using a template consisting of multiple piston elements, providing a curved template shape made up of a number of elements. This may provide a smoother transition from the center of cornea 50 to the edges and, thus, more precise and controlled myopia correction.

Figure 7:
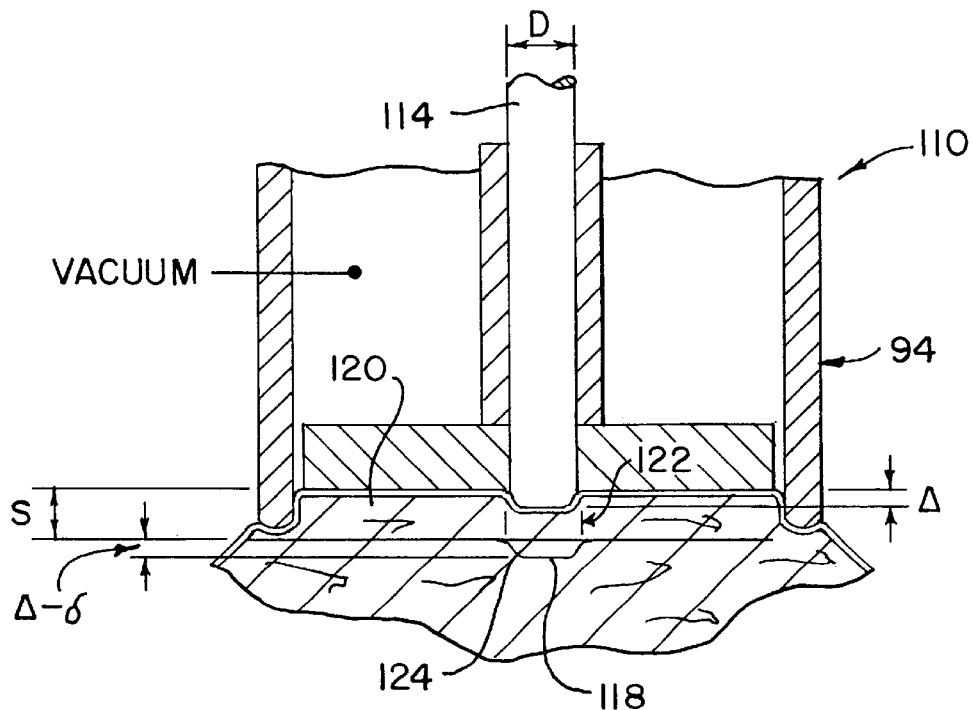
FIG. 7 is a schematic side view illustration of the FIG. 6 arrangement for removal of corneal tissue in position for a second cut of the microjet beam in accordance with the FIG. 5 embodiment of the present invention.

By displacing moveable template 48 downwards (posteriorly) along axis 55, after the first cut 56, a pre-shaped tissue may be cleaved from the underside of flap portion 44 rather than from stromal bed portion 46. In other embodiments of the present invention, a series of two non-planar cuts can be performed (e.g., first cut 56 and second cut 59 shown in a dotted line in FIG. 3, although the corresponding downward movement of the piston is shown in FIG. 7), displacing the movable template upwards and then downwards below its original position, or vice versa, to remove tissue both from stromal bed portion 46 and the underside of flap portion 44. The second cut 54 of the earlier embodiments is not necessary in this embodiment. This allows creation of thick inner cavities in cornea 50, for example, 200 µm or more, without excessive thinning of the stromal bed. Since the thickness and shape of a microjet cut in accordance with the present invention is adjustable, e.g., vernier adjustable, to a very high accuracy, e.g., 1 µm, the resultant cut can be controlled with great accuracy, for example, 4 µm or better. This enables removal of a thick lamellar layer with a reproducibility of better than a ⅓ diopter, even with the simple two-template embodiment shown in FIG. 3. This estimation takes into consideration possible inaccuracies in the scanning plane. By improving beam accuracy and template resolution, refraction changes in accordance with the present invention may be reproduced at even higher accuracies.

Figure 4:
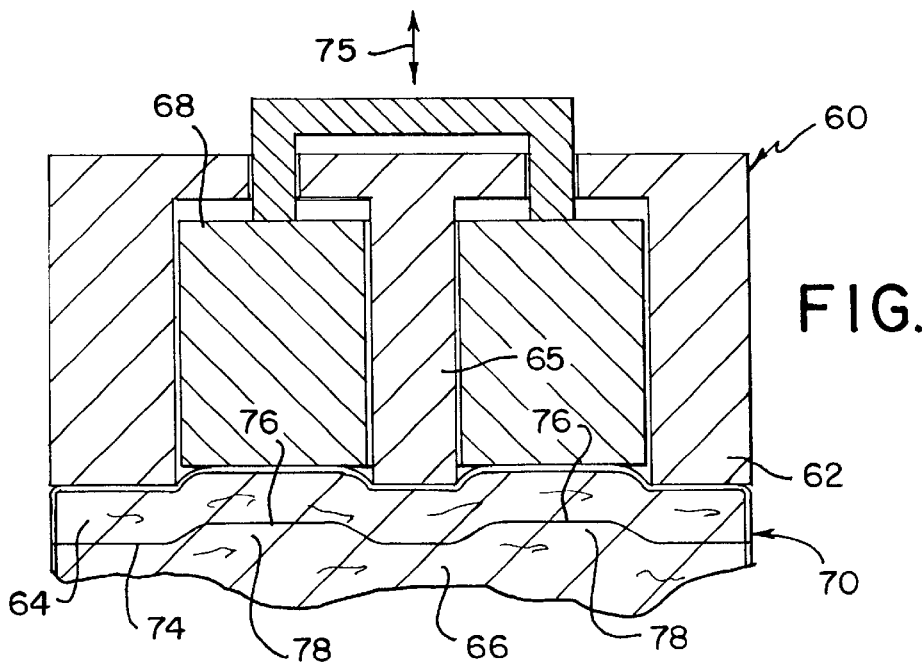
FIG. 4 is a schematic, side view, cross sectional illustration of part of a cornea and a vacuum template configured for cutting slabs of corneal tissue shaped for correction of hyperopia and astigmatism in accordance with a second alternative embodiment of the present invention.

FIG. 4 schematically illustrates a multiple vacuum template arrangement 60 adapted for removing a circular annulus of tissue 78, e.g., to correct hyperopia of a cornea 70. In the exemplary arrangement of FIG. 4, three templates elements are used, namely a fixed annular template 62, a middle moveable annular template 68 and a central fixed circular template 65 coplanar with the fixed annular template 62. The central fixed template 65 is connected to the template 62 in a cap arrangement at the top of the template 94. In addition, moveable template 68 contacts the anterior surface 72 of the cornea 70. This provides an interface of template arrangement 60 with the cornea surface 72 in a shape which resembles the annulus 78 to be removed. If annulus 78 is designed to be elliptical, correction for astigmatism is also possible. By moving template 68 upward along the axis indicated by arrows 75, a desired displacement is provided between a first cut 76 and a second cut 74 in cornea 70. As in the preceding embodiments, upper surface 72 of cornea 70 can be held by vacuum template arrangement 60 during the entire cutting process, i.e., the vacuum should not be released between the first and second cuts, but may be released if needed. The result of cuts 76 and 74 is an upper flap 64 and a stromal bed portion 66. The space between elements 62, 68 and 65 can be used to provide additional vacuum for holding top surface 72 of cornea 70. In some embodiments of the invention, the function of moveable template 68 is preformed by providing air pressure or partial vacuum in a predetermined area to control the extension of the tissue between cuts. Other aspects of hyperopia and or astigmatism correction in accordance with the present invention are generally analogous to those described above with reference to myopia correction and FIG. 3.

Figure 5:
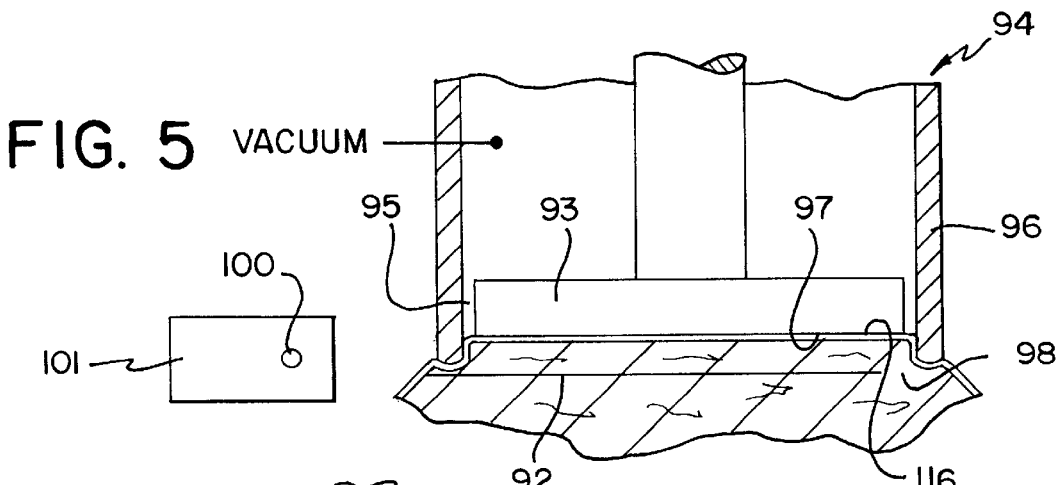
FIG. 5 is a schematic side view illustration of an arrangement for removal of corneal tissue using a microjet beam and a vacuum template in accordance with a third alternative embodiment of the present invention.

FIG. 5 illustrates an arrangement for removal of corneal tissue 91 using a liquid microjet beam cut line 92 and a flat vacuum template 94 according to another embodiment of the invention. The template 94 includes protective boundaries 96 also called a "vacuum guard" (which can also be referred to as a "vacuum trephine" or a traditional trephine cornea cutting tool with the edge contacting the cornea rounded so that it functions as a contact and support structure rather than a cutting structure) and a stationary template 93. The vacuum guard can be in the form of a ring 96 (which creates boundaries 96 in the side view illustration of FIG. 5). The stationary template 93 is oriented inside of the vacuum guard 96 but does not contact the vacuum guard 96. Rather, in this embodiment, there is a gap 95 between the vacuum guard 96 and the stationary template 93. In addition, a vacuum is created above the template 90 such that the gap 95 provides application of the vacuum to the cornea 91 in order to form a strong holding force so that the cornea anterior surface 116 conforms closely to the template lower surface 97. In alternative embodiments of the invention, gap 95 need riot be provided between the vacuum guard 96 and the stationary template 93. Rather, the stationary template 93 can be porous so that a sufficient vacuum is supplied by the template 93 to conform the cornea anterior surface 116 to the template lower surface 97. Accordingly, the invention is not dependent on the means of applying a vacuum to the cornea anterior surface 116.

Exemplary dimensions for the template 94 components are as follows: the diameter of the stationary template 116 is 9 mm and the cam 114 diameter is 1 mm. In addition, the inner diameter of the vacuum guard can be 9.2 mm, including a 0.1 mm gap around the template to enable it to fit but to allow a vacuum to be created. In further alternative embodiments, the stationary template can fit snugly inside the vacuum guard. However, the stationary template has grooves on its perimeter to provide vacuum channels.

Figure 6:
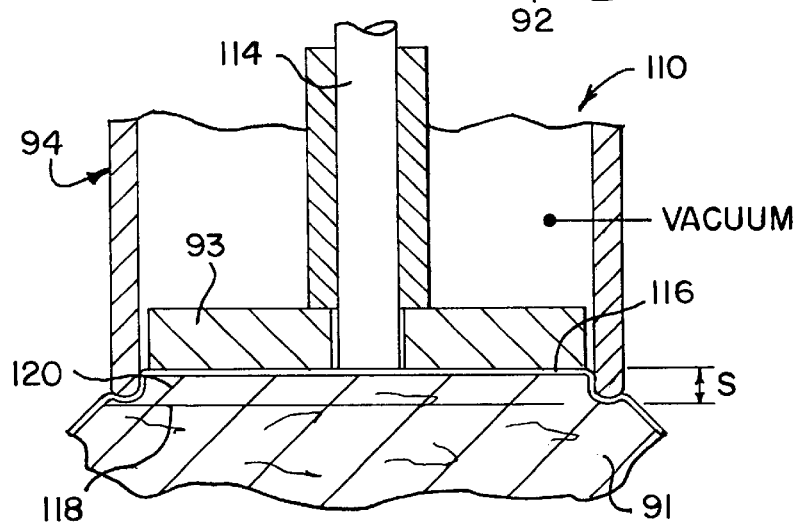
FIG. 6 is a schematic side view illustration of an arrangement for removal of corneal tissue using a microjet beam and a vacuum template including a piston or cam in position for a first cut of the liquid microjet beam in accordance with the FIG. 5 embodiment of the present invention.

The refractive correction procedure shown in FIGS. 5–7 is as follows: the first microjet cut 92 produces a hinged flap 98. The cornea 91 is applanated by the flat vacuum template 94 surrounded by the vacuum guard 96. The microjet 101 can have a beam scanning speed at a high value of 10–20 mm/second so that erosion associated with a cut is minimized and the cut is clean. Therefore, each cut can be completed in around 1 second such that the entire procedure can be completed in several seconds. Typically, a beam diameter of 33 $\mu$m at a stagnation pressure of 25 Kpsi is used. The cut plane 92 is parallel to the plane of the template 94 at an accurately set distance in the range 150–250 $\mu$m. The microjet beam begins the cut 92 and block 100 ends the cut 92 abruptly so that the hinge 98 remains. Consider that the cut 92 is completed and the template 94, scleral chuck (shown as 11 in FIG. 1; the scleral chuck allows the cornea to be immobilized as a base for holding the template 20), and the hinge 98 remain in place, the microjet beam 92 is turned off, and the nozzle assembly (not shown) is scanned back to its initial starting position. The scan 92 is repeated. In a mechanically stable, precise apparatus, the beam scans exactly in the plane of the first cut 92. It has been confirmed experimentally that under such circumstances no additional cutting occurs.

FIGS. 6 and 7 illustrate an arrangement for removal of corneal tissue 91 using a vacuum template 94 along with a piston or cam 114. The cam 114 is oriented in the interior of the stationary vacuum template 93, e.g., at the center of the stationary template 93. In this embodiment, the stationary vacuum template 93 assumes a ring shape with the cam 114 as its center. Initially, the surface of independently controlled cam 114 is coplanar with the stationary planar template surface 116 of the vacuum template 94. This is not essential for this technique to work although it is preferable. The cross-sectional shape of the cam 114 can be circular (not shown in this illustration). In alternative embodiments according to the invention, several different shapes may be used. The gap between the stationary template 93 and the cam 114 is small, just large enough to support a vacuum. The plane of the first microjet cut 118 is set at a distance S below the plane of the template 94. Therefore, S is the thickness of an upper flap 120 of the cornea 91 resulting from the first cut 118.

After the first cut 118, the cam 114 is translated downward a distance $\Delta$ into the anterior corneal surface (as shown in FIG. 7). Under the cam 114, and only under the cam 114, the plane of the initial cut 118 is pressed downward a distance, $\Delta - \delta$, in which $\delta/\Delta << 1$ and $\delta$ is the proximity correction as described below. The second cut 122 is therefore displaced $\Delta - \delta$ from the initial cut 118. The magnitude of $\delta$ increases with increase in S and decreases with increase in D, the diameter of the cam 114. The choice of S=200 $\mu$m and D=1 mm probably makes $\delta << \Delta$. However, in any cam array configuration, the change in $\Delta$ from one cam to an adjacent cam is usually small. This implies a larger effective value of D, hence, $\delta$ is reduced in any case. Nevertheless, if it is not negligible, its effect can be readily accommodated in any actual array-shaping algorithm.

As depicted in FIG. 7, there is a slight rounding 124 of the cut boundary 122 of the depressed interior volume under the cam 114. This rounding increases with S. When the second cut 122 is made, the microjet (not shown in FIG. 7) cuts in the same plane as the first cut 118, except for the section under the cam 114; the second cut 122 defines a new parallel cut interface surface for the depressed tissue volume. Following the cut 122, the tissue in this volume is no longer connected to the stromal bed or the underside of the upper flap 120. It is free and if it is thin, lamellar fragments are ejected by the microjet. If the free section is thick enough, it should have greater strength so that it comes out as a single piece. This is observed experimentally for 9 mm sections of 100 $\mu$m thickness which appear to be complete discs.

Shaping of the cornea as a result of the procedure illustrated in FIGS. 6 and 7 will now be described. The template 94 is removed and the cornea 92 becomes unconstrained. However, it has had tissue excised from the interface at the underside of the flap 120. The volume and shape of the excised tissue correspond almost precisely to the volume defined by the extension of cam 114. The smaller the value of S, the more closely the excised tissue volume approximates the extended volume. With the flap 120 in place, this excision will be reflected mostly as a relative depression in the anterior surface of the cornea 126 rather than the posterior cornea shape. In removal over a large area, the excised volume induces a change in the anterior surface shape because the underlying stromal bed is so much thicker than the flap and no tissue is removed from the bed. Hence, the posterior surface of the cornea and the stromal bed surface maintain essentially their original shape. The flap 120 deforms and fills in the excised volume. The same issue of deformation arises in LASIK. It is the anterior surface that changes because the photoablation layer is much closer to the anterior surface. The essential difference is that in LASIK, the tissue is removed from the stromal bed rather than the flap 120. It has been reported that for large corrections, the thinning and weakening of the stromal bed can lead to keratoectasia. This is avoided in the microjet technique by virtue of the fact that the tissue is removed from the underside of the flap. However, for large corrections, it may be desirable to remove tissue from both the underside of the flap and from the stromal bed.

In addition, the microjet cut 118 is always at the local lamellar interface, since the mechanism of the microjet cut is to strip away sections of lamellae. (The laser photoablation has the same characteristic.) Hence, the plane of the microjet cut is indeterminate to the thickness of the lamellae.

The maximum lamellar thickness is about 2 μm, hence the associated thickness ambiguity, ±2 μm, is trivial.

In an alternative embodiment of the present invention, the cam 114 can be recessed by raising it away from the anterior surface rather than lowering it to achieve extension. The result can be virtually identical to the FIGS. 6 and 7 procedure except that the excised tissue is removed from the stromal bed 121 interface rather than from the underside of the flap 120. All other considerations are the same. Since for accuracy, it is desirable to minimize S, it is probably more appropriate to remove tissue from the flap 120. The risk of ectasia for large corrections is reduced. Hence, extending the cam 114 into the anterior cornea surface is more desirable.

Figure 8:
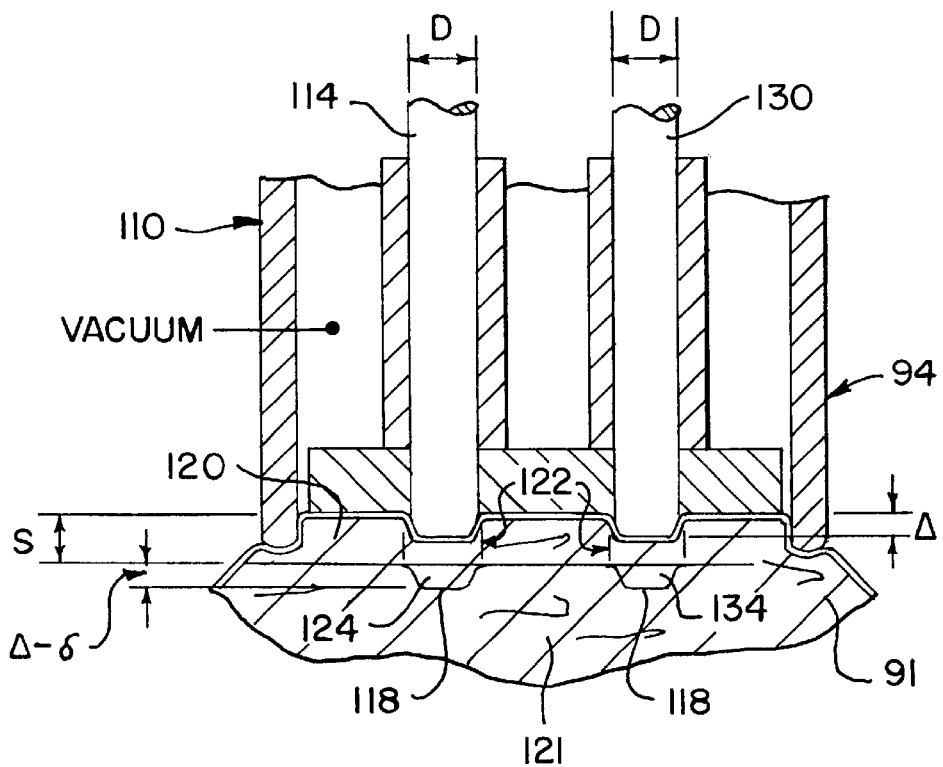
FIG. 8 is a schematic side view illustration of an arrangement for removal of corneal tissue using a liquid microjet beam and a vacuum template including multiple pistons or cams for translation downward or upward relative to the anterior cornea surface in accordance with a fourth alternative embodiment of the present invention.

FIG. 8 is a schematic side view illustration of an arrangement for removal of corneal tissue using a liquid microjet beam and a vacuum template along with multiple pistons or cams (for example, two cams 114 and 130 are shown). The cams 114 and 130 can translate downward or upward relative to the anterior cornea surface. Each of the cams 114 and 130 can operate in the same manner as cam 114 to excise tissue from portions of the cornea 91. For example, cam 130 can produce excisable tissue by a first cut 118 followed by a second cut 122 of the liquid microjet. In addition, as in the FIG. 7 embodiment, cams 114 and 130 can recess (not shown) in order to remove tissue from the stromal bed 121 rather than from the underside of the flap 120. In addition, in alternative embodiments, the distances Δ of movement of cams 114 and 130 can be different. The operation of each cam 114 and 130 relative to the other does not limit the scope of the invention. Rather, their operation depends on the refractive correction objective of the procedure.

Figure 9:
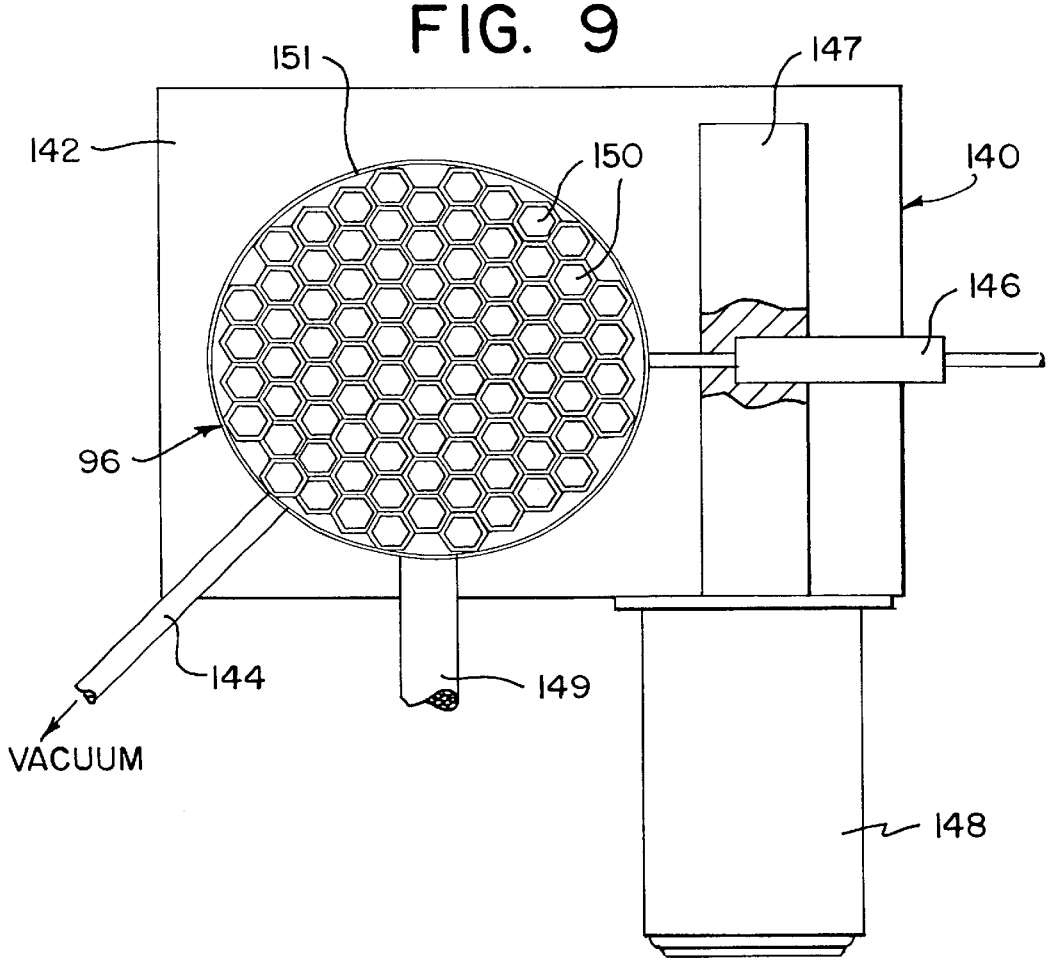
FIG. 9 is a schematic bottom view illustration of an arrangement for removal of corneal tissue using a microjet beam and a vacuum template including multiple pistons or cams according to a fifth embodiment of the present invention.
Figure 10:
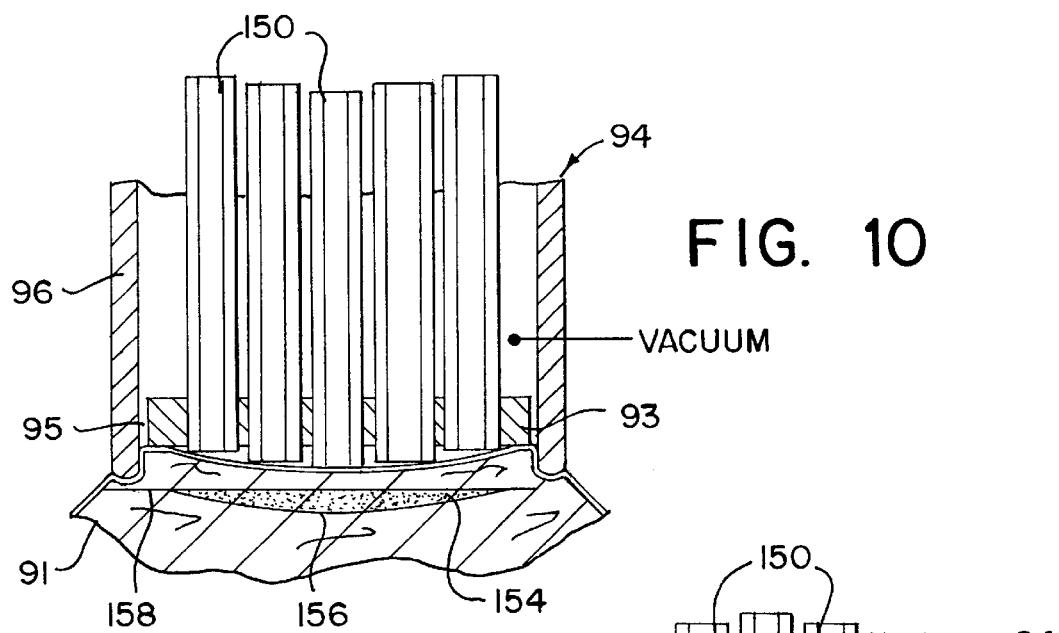
FIG. 10 is a schematic side view illustration of the FIG. 9 embodiment where there arc five pistons or cams and the corneal tissue removal device is applied to a cornea for a second cut in order to correct myopia according to the fifth embodiment of the present invention.
Figure 11:
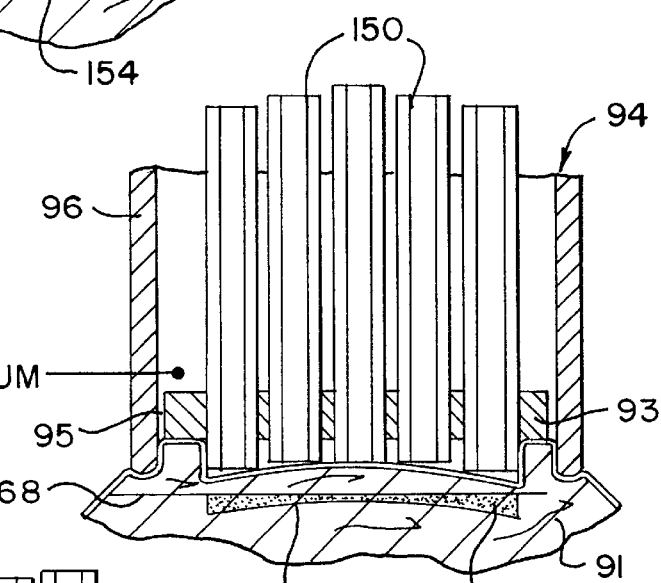
FIG. 11 is a schematic side view illustration of the FIG. 9 embodiment where there are five pistons and the corneal tissue removal device is applied to a cornea for a second cut in order to correct hyperopia according to the fifth embodiment of the present invention.

To complete the discussion of the basic technique, the origin of the proximity effect is described next. The cornea 91, while nominally incompressible because it is made up of mostly water-based fluid, is actually locally compressible. When the cornea 91 is applanated in a localized area, corneal fluid may move laterally into the immediate region surrounding the applanation. Thus, a localized edema (observed by the ophthalmologist when pushing on the cornea) is created in the surrounding region. This edema surrounding the local applanation region is the origin of the observed light backscatter or haze seen when pressing on the cornea. The result of the fluid motion away from the applanation is a local thinning of the cornea 91 and a thickening in the surrounding aimulus. Thus, a motion downward of the anterior surface into the cornea 91 is not reflected fully in an equivalent downward motion of the posterior surface. This is also the case at any intermediate plane. The closer to the anterior surface, the smaller is the effect. The larger the diameter of the local applanation region, the smaller this effect. The deviation from one-to-one extension under a local applanation is called the proximity effect. In an array, with respect to a given cam 114, an adjacent cam 130 (shown in FIG. 8) or additional cams (as shown in FIGS. 9–11) may applanate a similar amount, effectively increasing the lateral extent of the applanation region and reducing the proximity effect. In any case, this correction may be calculated once the proximity effect is characterized. Hence, shaping corrections can be applied if necessary. The mechanical aspects of the cornea are not well characterized; accordingly, this analysis is done empirically.

FIG. 9 is a schematic bottom view illustration of an arrangement 140 for removal of corneal tissue using a microjet beam (not shown) and a vacuum template 96 (shown and further described in FIG. 9A) including multiple pistons or cams 150 according to a fifth embodiment of the present invention. The vacuum template 151 is supported on a base plate 142 and the vacuum is provided by a vacuum cable 144. The microjet 146 is positioned by use of a scan guide 147 and can be powered by a linear motor 148. In addition, the movement of the cams 150 in the vacuum template can be controlled by a control cable 149. The FIG. 9 illustration is exemplary of a device for implementing the corneal tissue removal using one or more cams 150 which shape the anterior surface of the cornea, a microjet 146 for cutting the corneal tissue and the devices used to control the cams 150 and the micro jet 146. The devices 142, 144, 147, 148 and 149 may be conventional.

Figure 9A:
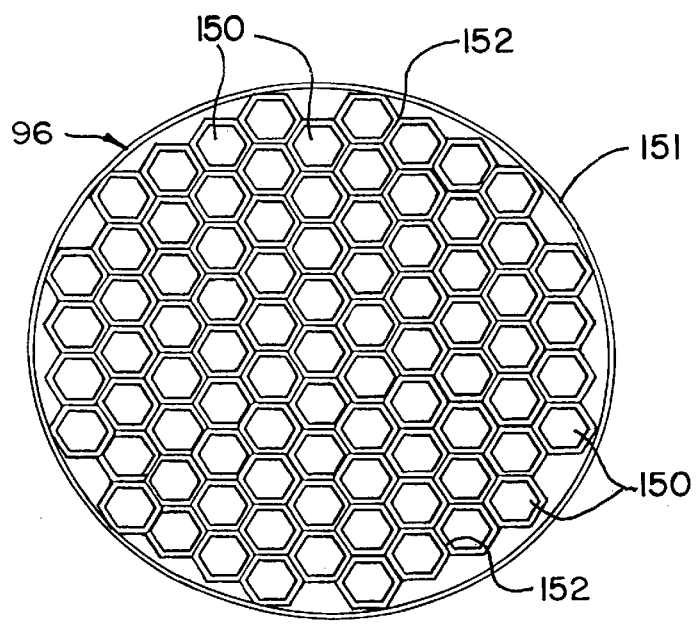
FIG. 9A is a schematic cross sectional illustration of the multiple pistons or cams of FIG. 9 according to the fifth embodiment of the present invention.

FIG. 9A is a schematic cross-sectional illustration of the multiple pistons or cams for a vacuum template used in the apparatus of FIG. 9. A multiplicity of pistons 150, hexagonal in cross section, are placed in a honeycomb array to form the template 151 within the vacuum guard boundary 96. Small gaps 152 between cams 150 allow access to the vacuum (not shown) above the template. The cams 150 may be piezoelectric pistons which are under computer control to provide any variety of shapes to custom shape the anterior surface of the cornea. The exemplary structure of FIG. 9A includes 11 rows of cams 150, those rows including from left to right the following number of cams 150: 4, 7, 8, 8, 9, 10, 9, 10, 9, 8, 7 and 4. There are many ways to arrange the cam 150. The length of the piezoelectric pistons 150 will vary depending upon the material from which they are made, but can be several centimeters long to achieve an extension of 100 μm. Magnetostriction may also work. The piezoelectric construction may be a single, shaped rod of piezoelectric ceramic, or a stack of alternating, reverse-polled, ceramic discs or other piezoelectric materials etc. The latter construction allows low voltage operation from integrated circuit drivers. One end of each piston is made coplanar with the others. The other end of the piston is free and, in the absence of applied voltage, is approximately coplanar with the others. The invention does not require precise co-planarity. Only the extension of the piston with voltage needs to be accurately controlled. Exactly where the end of the piston starts from is not so important. It might be desirable to program the amplifiers of the driver array to ensure that extension versus input voltage for each piston is the same. To ensure the utmost accuracy, temperature can be determined and inputted. A simple truth table built into the electronics will serve to produce submicron accuracy for the template shape. Such truth tables are known to those of ordinary skill in the art and will therefore not be further described herein.

FIG. 10 is a schematic side view illustration of an arrangement for removal of corneal tissue using a microjet beam and a vacuum template 94 including the multiple cams 150 shown in FIG. 9 in position for a second cut of the liquid microjet beam for correction of myopia. The template includes the vacuum guard 96 and the stationary template 93 separated by gap 95. Five cams 150 are shown in this embodiment. The cams 150 are extendable downward into the anterior of the cornea 91. The shaded area indicates a volume of excised tissue 154 such that a first cut 156 has already occurred and the cams 150 are in position for a second cut 158, which is shown in FIG. 10. The excised tissue 154 is a crescent shaped (plano-convex) volume internal to the stroma from the posterior side of the flap created by the first cut 156. When the cornea 91 is allowed to resume its normal shape after the template is removed and the flap is smoothed and flattened (juxtaposed) against the stromal bed, the anterior corneal surface is flattened relative to its original shape. The radius of curvature of the new surface is greater than that of the original surface leading to a reduction in refractive power. This corresponds to a correction for myopia.

FIG. 11 is a schematic side view illustration of an arrangement for removal of corneal tissue using a microjet beam and a vacuum template 94 including the multiple cams 150 shown in FIG. 9 in position for a second cut of the liquid microjet beam for correction of hyperopia. FIG. 11 includes the same components as FIG. 10, but the position of the cams 150 in FIG. 11 is adjusted such that custom shaping for correction of hyperopia is achieved. As a result, the first and second cuts 166 and 168, respectively, cause the resulting excised tissue volume 164 to differ in shape from the volume 154 in FIG. 10. The tissue 164 is a piano-concave volume taken from the posterior side of the flap. This leads to a steepening of the anterior surface of the cornea 91 and an increase in the radius of curvature. It increases refractive power and corrects for hyperopia. Otherwise, FIG. 11 operates in the same manner as FIG. 10. In general, FIGS. 10 and 11 illustrate how an array of cams 150 can be used to create custom changes in the shape of the cornea 91 for different purposes.

Figure 12:
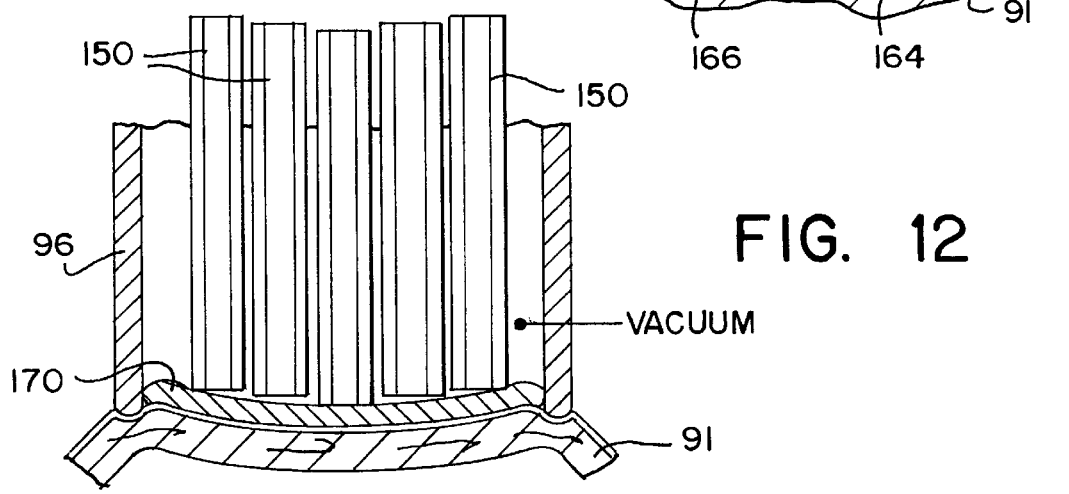
FIG. 12 is a schematic side view illustration of the FIG. 9 embodiment where there are five pistons including a disc or membrane at the contact point with the cornea and the corneal tissue removal device is applied to the cornea for a second cut according to the fifth embodiment of the present invention.

FIG. 12 is a schematic side view illustration of the FIG. 9 embodiment where there are five pistons 150 including a disc or membrane 170 at the contact point with the cornea 91 and the corneal tissue removal device is applied to the cornea for a second cut. More particularly, the free end of the cam 150 array can be covered with a thin, precision thickness, disc 170 made from a flexible membrane that has micro-channels (not shown). The membrane disc 170, with a serrated, perimetric boundary, fits inside the vacuum guard directly against the cam array 150. The microchannels in the membrane serve to create the vacuum interface surface. The membrane serves as an insulating barrier between the cam array and the cornea. The flexible nature of the membrane smooths the transition between elements. The surgical nature of the function makes it desirable that the membrane be a disposable element. Examples of materials for the disc include sintered thin soft metal, porous rubber, woven fabric etc.

Common vision errors can be corrected under computer control of the cams 150. For example, a cylinder shape for the excised volume achieved with a predetermined configuration of the cams 150 and the two cut approach could be used to correct astigmatism. Accordingly, the present invention is not limited to the custom shapes or types of correction shown herein. Rather, any shape consistent with the number and density of cams 150 is attainable with multiple pistons such that the present invention applies to currently known and hereinafter discovered correction procedures which involve altering the shape of the cornea. For example, changing the shape without a change in central curvature would also allow a change in the sphericity of the anterior surface. Corrections for common lens aberrations such as coma and spherical aberration become possible. This allows improvement of best-corrected visual acuity if the nature of the necessary change can be specified.

The procedures described above show both an elegant and practical approach to achieve refractive change. In accordance with the present invention, unlike prior art multiple cut ALK and HRK techniques, there is no need to move the flap out of the way for the second cut. Additionally, the refractive change in accordance with the present invention is vernier adjustable. It has been shown that this procedure is highly accurate and highly reproducible and is automatically and accurately centered. The diameter of the slab of inner corneal tissue that is removed need not be very large because of the accurate centering enabled by the invention. The boundary transition may be smooth, limiting scattering of light and the glare effects it produces.

It will be appreciated by persons skilled in the art that the present invention is not limited to the specific embodiments described herein with reference to the accompanying drawing. Rather, the scope of the present invention is limited only by the following claims:

What is claimed is:

1. A method of removing inner corneal tissue with a fluid beam comprising the steps of:
   establishing an anterior surface of a cornea in a first configuration;
   scanning the fluid beam across the cornea to produce a first cut in the cornea;
   establishing the anterior surface of the cornea in a second configuration; and
   scanning the fluid beam across the cornea to produce a second cut in the cornea,
   wherein a volume of inner corneal tissue included between said first and second cut boundaries is removed.

2. A method according to claim 1 used for refractive correction, wherein said removed volume of corneal tissue by virtue of its shape has refractive power that corresponds to a desired change of the refraction properties of said cornea.

3. A method according to claim 2 wherein said refractive correction comprises correction of one of myopia, hyperopia, astigmatism, myopia with astigmatism and hyperopia with astigmatism.

4. A method according to claim 1 wherein the first configuration and the second configuration are one of different from and the same as each other.

5. A method according to claim 1 wherein one of the first configuration and the second configuration is non-planar.

6. A method according to claim 1 wherein both of the first configuration and the second configuration are non-planar.

7. A method according to claim 1 and further comprising, before the step of scanning the fluid beam across the cornea to produce a second cut in the cornea, the step of causing displacement of the fluid beam is in a direction perpendicular to the plane defined by the direction of the fluid beam and the direction of scanning.

8. A method according to claim 1 wherein said volume of corneal tissue has a first surface parallel to the plane defined by said first configuration and a second surface parallel to the plane defined by said second configuration.

9. A method according to claim 1 wherein the steps of maintaining the anterior surface of the cornea in said first and second configurations comprise the steps of engaging the anterior surface of said cornea with first and second configurations, respectively, of a vacuum template.

10. A method of removing inner corneal tissue with a fluid beam comprising the steps of:
    maintaining an anterior surface of a cornea in a predetermined configuration;
    scanning the fluid beam across the cornea to produce a first cut in the cornea;
    causing displacement of the fluid beam relative to the plane defined by the first cut in the cornea;
    scanning the fluid beam across the cornea to produce a second cut in the cornea,
    wherein a volume of inner corneal tissue included between said first and second cut boundaries is removed.

11. A method according to claim 10 wherein the displacement of the fluid beam is in a direction perpendicular to the plane defined by the direction of the fluid beam and the direction of scanning and the plane of the fluid beam after its displacement is parallel to the plane of the fluid beam for the first cut, whereby said volume of corneal tissue has substantially parallel surfaces.

12. A method of removing inner corneal tissue with a fluid beam comprising the steps of:

establishing an anterior surface of a cornea in a first configuration by a vacuum template, said vacuum template including at least one piston which contacts a portion of said anterior surface of the cornea;

scanning the fluid beam across the cornea to produce a first cut in the cornea;

establishing the anterior surface of the cornea in a second configuration by said piston moving in a direction perpendicular to the plane defined by the direction of the fluid beam and the direction of scanning, whereby said piston maintains contact with the anterior surface of the cornea so that the anterior surface of the cornea is changed in shape to reflect the second configuration of said piston; and scanning the fluid beam across the cornea to produce a second cut in the cornea, wherein a volume of inner corneal tissue included between said first and second cut boundaries is removed.

13. A method according to claim 12 wherein said vacuum template includes a plurality of pistons and said establishing the anterior surface of the cornea in a second configuration step further includes each of said plurality of pistons moving in a direction perpendicular to the plane defined by the direction of the fluid beam and the direction of scanning and maintaining contact with the anterior surface of the cornea, and, for each of said plurality of pistons, the direction of movement is opposite from the direction of movement of at least one other of said plurality of pistons and the magnitude of movement is different than the magnitude of movement of at least one other of said plurality of pistons, whereby the anterior surface of the cornea is changed to a custom shape to reflect the second configuration of said plurality of pistons.

14. A method according to claim 12 used for refractive correction, wherein said removed volume of corneal tissue by virtue of its shape has refractive power that corresponds to a desired change of the refraction properties of said cornea.

15. A method according to claim 14 wherein said refractive correction comprises correction of one of myopia, hyperopia, astigmatism, myopia with astigmatism and hyperopia with astigmatism.

\* \* \* \* \*